(12) United States Patent (10) Patent No.: US 7,702,063 B2
Koehler et al. (45) Date of Patent: Apr. 20, 2010

(54) CT METHOD FOR THE EXAMINATION OF CYCLICALLY MOVING OBJECT

(75) Inventors: Thomas Koehler, Norderstedt (DE); Michael Grass, Buchholz in der Nordheide (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 413 days.

(21) Appl. No.: 11/719,305

(22) PCT Filed: Nov. 7, 2005

(86) PCT No.: PCT/IB2005/053635

§ 371 (c)(1),
(2), (4) Date: May 15, 2007

(87) PCT Pub. No.: WO2006/051467

PCT Pub. Date: May 18, 2006

(65) Prior Publication Data

US 2009/0074129 A1 Mar. 19, 2009

(51) Int. Cl.
*A61B 6/00* (2006.01)
(52) U.S. Cl. .............................................. 378/4; 378/8
(58) Field of Classification Search ...................... 378/4, 378/8
See application file for complete search history.

(56) References Cited

U.S. PATENT DOCUMENTS

| 6,215,519 B1 | 4/2001 | Nayar et al. |
| 6,324,243 B1 | 11/2001 | Edic et al. |
| 6,757,008 B1 | 6/2004 | Smith |

(Continued)

FOREIGN PATENT DOCUMENTS

EP 1436782 B1 11/2006

(Continued)

OTHER PUBLICATIONS

Manzke et al., Automatic phase point determination for cardiac CT imaging, Medical Imaging, 2004, Proceedings of SPIE, vol. 5370, pp. 690-700.*

(Continued)

*Primary Examiner*—Edward J Glick
*Assistant Examiner*—Alexander H Taningco

(57) ABSTRACT

The invention relates to a computer tomography method for the detection of a cyclically moved object in an examination zone. First, after the acquisition of the measured values, a rough image of the examination zone is reconstructed from which a region relevant for the further method is selected. For the generation of an image with reduced motion artifacts or improved temporal resolution, reconstruction windows in predefinable position are used, which are optimized in such a way that they are, on the one hand, smallest possible, on the other hand, however, sufficiently large, to be able to reconstruct all voxels of this region. Only measured values acquired within the reconstruction windows are taken into account for the reconstruction of a CT image of the region.

19 Claims, 3 Drawing Sheets

U.S. PATENT DOCUMENTS

Figure 1:
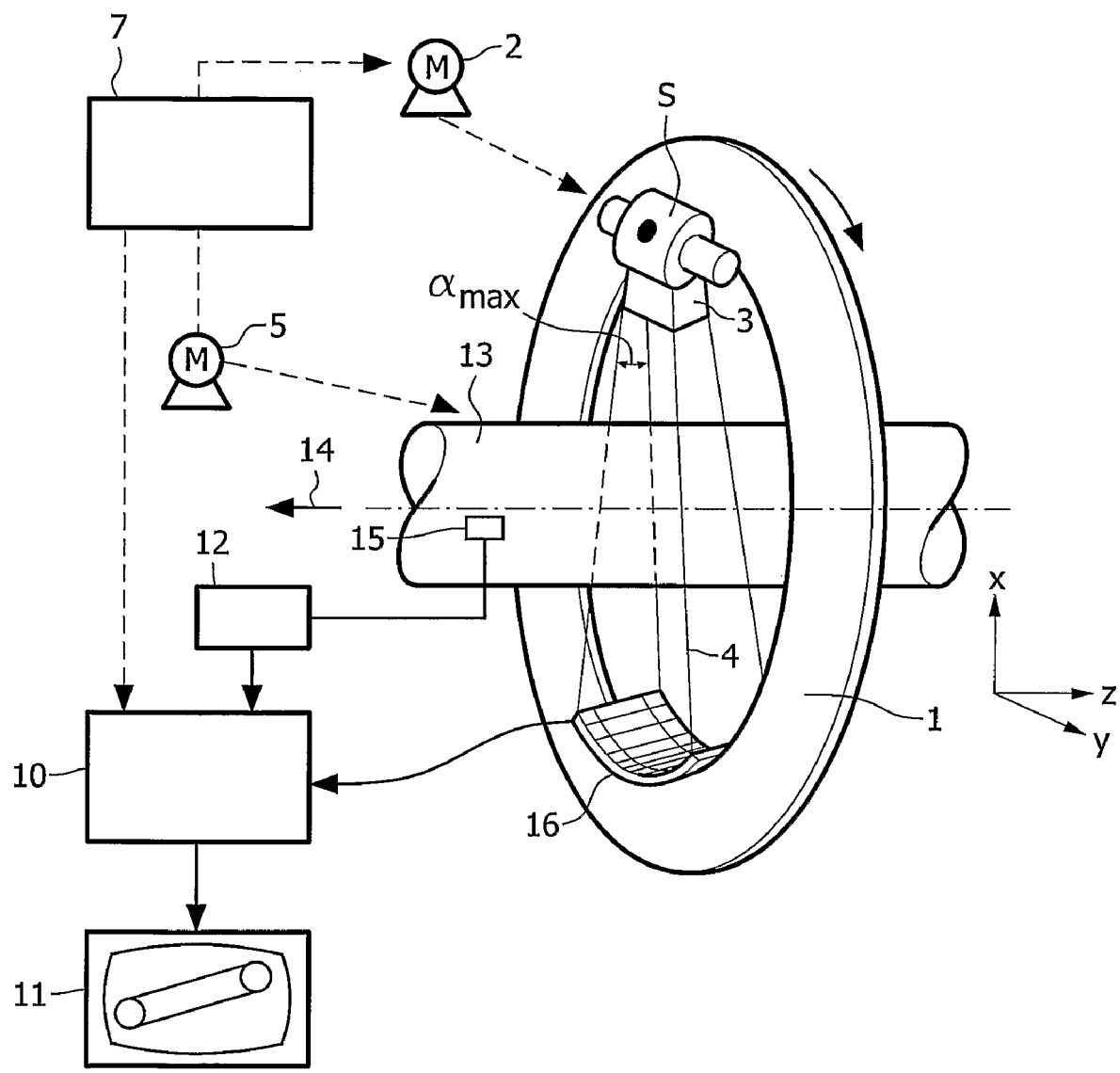

| | | | |
|---|---|---|---|
| 6,865,248 B1* | 3/2005 | Rasche et al. .................. | 378/8 |
| 6,879,656 B2* | 4/2005 | Cesmeli et al. ................ | 378/4 |
| 2002/0025017 A1* | 2/2002 | Stergiopoulos et al. ........ | 378/8 |
| 2002/0196894 A1* | 12/2002 | Launay et al. ................. | 378/8 |
| 2003/0092983 A1 | 5/2003 | Baker et al. | |
| 2003/0220558 A1 | 11/2003 | Busse | |
| 2004/0081269 A1* | 4/2004 | Pan et al. ....................... | 378/4 |
| 2004/0082846 A1 | 4/2004 | Johnson et al. | |
| 2004/0120449 A1 | 6/2004 | Edic et al. | |
| 2004/0175024 A1* | 9/2004 | Rasche et al. ............... | 382/128 |
| 2004/0202283 A1 | 10/2004 | Okumura et al. | |
| 2007/0003016 A1* | 1/2007 | Brunner et al. .......... | 378/98.12 |

FOREIGN PATENT DOCUMENTS

WO     WO 2004075115 A1 * 9/2004

OTHER PUBLICATIONS

Manzke, R., et al.; Adaptive temporal resolution optimization in helical cardiac cone beam CT reconstruction; 2003; Med. Phys.; 30(12)3072-3080.

* cited by examiner

CT METHOD FOR THE EXAMINATION OF CYCLICALLY MOVING OBJECT

The invention relates to a computer tomography method for the detection of an examination zone, which is exposed at least partly to a cyclical movement. In addition, the invention relates to a computer tomograph for the execution of such a method as well as a computer program for controlling such a computer tomograph.

During the examination of a cyclically moving object, for example, the heart of a patient, it is disturbingly noticeable that the time, which the radiation source of a computer tomograph needs for a rotation around the examination zone, is not negligibly short in comparison with the duration of a heart cycle. Therefore, if one tried to reconstruct a CT image (CT=Computer Tomography) of the heart from the measured values, which were acquired during a single rotation, then this CT image would be afflicted with strong motion artifacts, because the measured values, which are taken into account for the reconstruction, were acquired in different movement phases.

In order to reduce these motion artifacts, the measured values are not acquired during a single rotation, but during a number of rotations, so that each individual voxel is irradiated by the radiation source in several rotations. Then, parallel to the acquisition of the measured values, a signal representing the cyclical movement, particularly an ECG signal is recorded, so that the temporal allocation between the individual heart cycles and the acquisition of the measured values can be detected and stored. The radiation source then usually emits a conical beam, which is detected with a two-dimensional detector arrangement (comprising several detector rows) in connection with a helical relative movement between the examination zone and the radiation source.

The reconstruction then does not usually take place for the entire irradiated volume, but only for a pre-determined area, which is so large that the heart is safely included therein. For the reconstruction only the measured values are taken into account that have been acquired within the heart cycles in time periods in which the heart has moved relatively little, which can be determined by means of the ECG signal. These time periods, designated below as reconstruction windows, can be shorter than the time needed for a rotation of the radiation sources, so that fewer motion artifacts occur in the reconstructed CT image, although the acquisition of the measured values essentially takes longer than a single rotation of the radiation source. The selection of measured values in specific reconstruction windows, which is known among experts as retrospective gating, can take place in a different way:

With a first approach known from EP-A-1 436 782, a number of low-resolution 3D images are generated from the measured values, from which images movement information for individual areas of the heart is derived. Depending on this, for each of these areas individually, which areas can also comprise a single volume element (called voxel below for short), reconstruction windows of a specific size and position within the heart cycle are determined. Only the measured values, which were acquired within these reconstruction windows, are taken into account for the reconstruction. In principle, CT images with the fewest possible motion artifacts can be reconstructed with them, but this approach is at present not yet viable because of its immense demands on the computing power.

With another approach, which is described in a publication of Manzke et al. in Med. Phys. 30 (12), December 2003, pages 3072-3080, the cost of computation is reduced considerably, in that reconstruction windows are determined in a predefinable position within the heart cycles, which windows apply to all voxels in the volume to be reconstructed. These reconstruction windows are optimized in such a way that they are, on the one hand, smallest possible, but on the other hand, so large that each voxel in the volume to be reconstructed within the reconstruction windows is exposed to radiation from an angle range (180°) sufficient for the reconstruction. The invention emanates from this method. It is an object of the invention to improve the temporal resolution that can be achieved with that of the reconstructed CT image or to reduce the motion artifacts respectively.

This object is achieved in accordance with the invention by a computer tomography method for the detection of an examination zone, which is exposed at least partly to a cyclical movement, which method comprises the following steps:

a) Generation of a beam traversing the examination zone with a radiation source rotating several times around the examination zone, b) Acquisition of a set of measured values, which depend on the intensity of the beam beyond the examination zone, with a detector unit during the rotation of the radiation source with simultaneous recording of a signal representing the cyclical movement, c) Reconstruction of a rough image from the measured values, d) Selection of a region within the area represented by the rough image, e) Optimization of reconstruction windows in predefinable position within the movement cycles in such a manner that the reconstruction windows are, on the one hand, smallest possible and, on the other hand, so large that each voxel of the region within the reconstruction windows is struck by the beam from an angle range sufficient for the reconstruction, f) Reconstruction of an image of the region from the measured values acquired within the reconstruction windows.

As a result of the previous reconstruction (naturally flawed by strong artifacts) of a rough image from the measured values—independent of their position within a heart cycle—and as a result of the selection of a region within the rough image relevant for the diagnosis—for example of the heart—it is possible to limit the subsequent reconstruction to the smallest possible volume with retrospective gating. But, the less the voxels that have to be considered for the optimization of the reconstruction windows within the movement cycles, the smaller the reconstruction windows can be and the better the temporal resolution is of the reconstructed CT image or the fewer its motion artifacts respectively. Thereby, the best possible image quality is achieved, which is attainable with a method with equal reconstruction windows for all voxels to be reconstructed.

In another embodiment, a method allows a faster acquisition of the measured values than with a method with which a planar, fan-shaped beam is detected by a detector arrangement with only a single detector row.

In another embodiment, a method makes it possible to examine larger segments in the direction of the axis of rotation. Basically, such a segment could, in fact, also be detected with a circular relative movement, with which examination zone and radiation source do not displace relatively to each other, however this would require a detector arrangement with a correspondingly high number of detector rows, which would lead to additional reconstruction errors outside the plane in which the radiation source moves.

In another embodiment, if the rough image within which the region should be selected has a reduced spatial resolution, less computing power is necessary or less computing power is needed for the reconstruction of the rough image respectively.

Another embodiment makes allowances for the fact that as a rule only two-dimensional areas (layers) are reconstructed. If the optimization is limited to the voxels within such a two-dimensional area, this may lead to a further decrease of the reconstruction windows and therewith to a further decrease of the motion artifacts or an improvement of the temporal resolution respectively. However, the optimization would have to be executed again for other layers. Insofar it is simpler if the optimization is carried out for a three-dimensional area, from which subsequently arbitrarily oriented layer images can be reconstructed.

In another embodiment, the radiation exposure in the examination zone is reduced. Another embodiment produces a representation of the examination zone associated with better-defined outlines or with fewer motion artifacts.

In other embodiments, a computer tomograph for the execution of the method in accordance with the invention and a computer program suitable for such a computer tomograph.

These and other aspects of the invention are apparent from and will be elucidated with reference to the embodiments described hereinafter, though the invention should not be considered to be limited to these.

Figure 2:
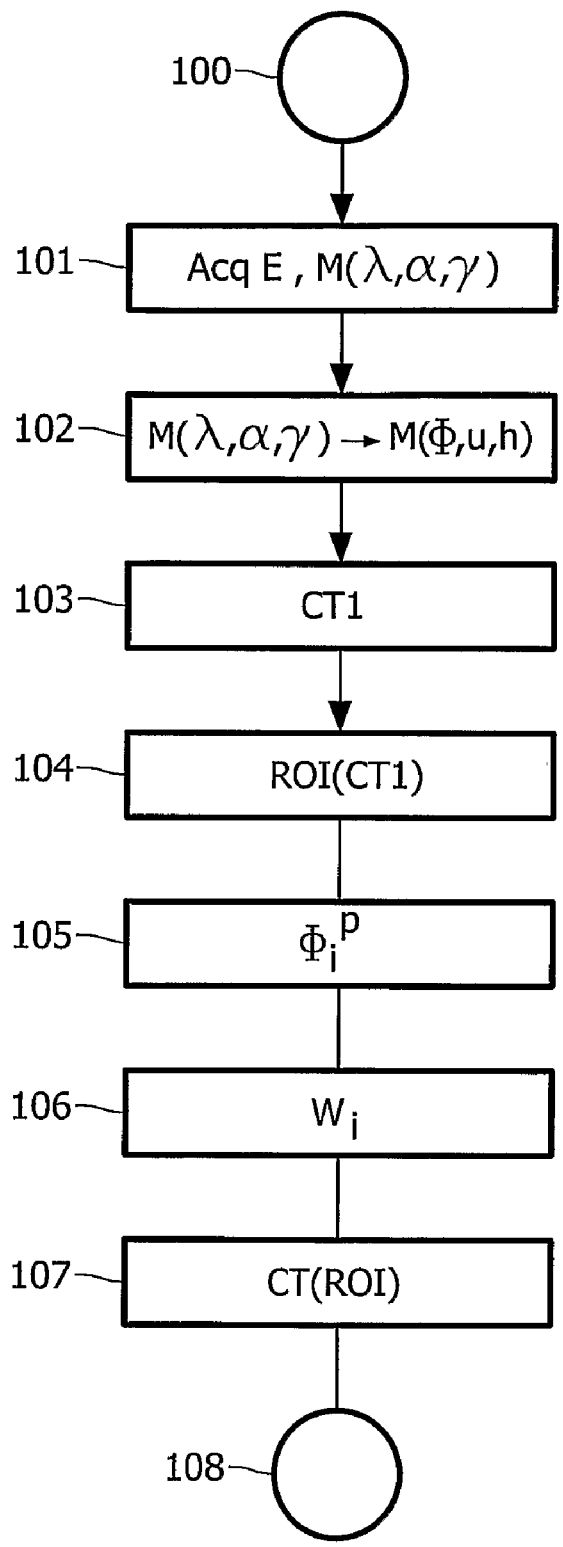
Figure 3:
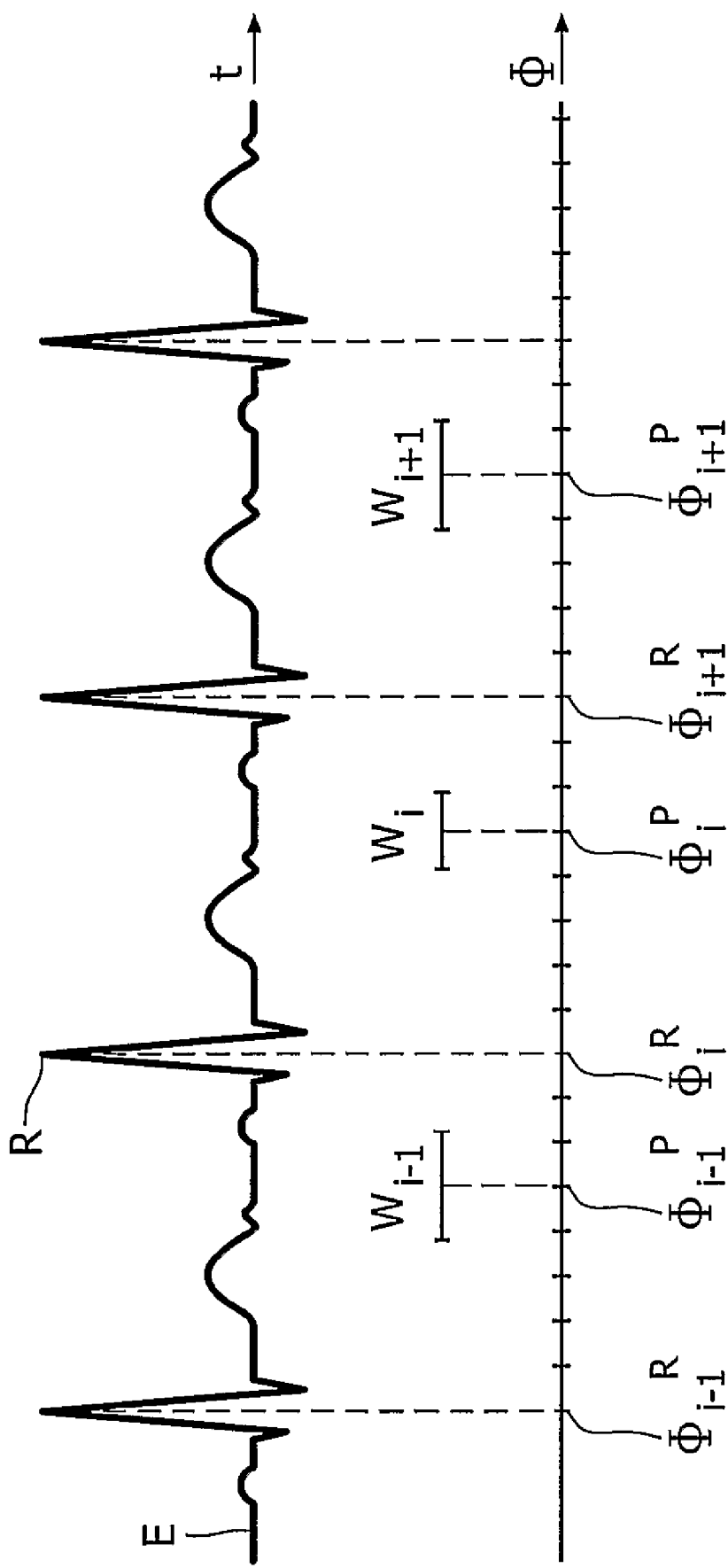

In the drawings:

FIG. 1 shows a computer tomograph with which the method in accordance with the invention can be executed, FIG. 2 shows a flow chart of the method in accordance with the invention and FIG. 3 shows the allocation between a signal representing the cyclical movement of the heart and the acquired measured values.

The computer tomograph represented in FIG. 1 comprises a gantry 1, which can rotate around an axis of rotation 14 that runs parallel to the z-direction of the x, y, z-coordinate system represented in FIG. 1. In addition, the gantry is driven by a motor 2 with a preferably constant, but adjustable angular speed. A radiation source S, for example, an X-ray device, is fastened to the gantry. This is provided with a collimator arrangement 3, which forms a conical beam 4 from the radiation generated by the radiation source S, that is, a beam that has a finite expansion different from zero, both in z-direction and in a direction perpendicular to it (that is, in a plane perpendicular to the axis of rotation).

The beam 4 penetrates an examination zone 13, in which an object, for example a patient, can be located on a patient examination table (neither represented further). The examination zone 13 has the form of a cylinder. After passing through the examination zone 13 the X-ray beam 4 strikes a two-dimensional detector unit 16 fastened to the gantry 1, which detector unit comprises a number of detector rows with a respective multiplicity of detector elements. The detector rows are located in planes perpendicular to the axis of rotation, preferably on a circular arc around the radiation source S. They may, however, be formed differently, for example, describe a circular arc around the axis of rotation 14 or be rectilinear. Each detector element struck by the beam 4 provides a measured value for a ray from the beam 4 in each position of the radiation source.

The aperture angle of the beam 4 designated as $\alpha_{max}$ (aperture angle is defined as the angle enclosed by a ray, located in a plane perpendicular to the axis of rotation 14 on the edge of the beam 4, with a plane defined by the radiation source S and the axis of rotation 14) determines the diameter of the object cylinder, within which the object to be examined is located when the measured values are acquired. The examination zone 13—or the object or the patient examination table—can be moved parallel to the axis of rotation 14 or to the z-axis by means of a motor 5. Equivalently, however, the gantry could also be moved in this direction.

If the motors 5 and 2 run simultaneously, the radiation source S and the detector unit 16 describe a helical trajectory relative to the examination zone 13. If, on the other hand, the motor 5 for the feed in z-direction stands still and the motor 2 causes the gantry to rotate, a circular trajectory results or a relative movement for the radiation source S and the detector unit 16 relative to the examination zone 13.

The measured values acquired by the detector unit 16 are supplied to an image-processing computer 10, which reconstructs a CT image from them, that is, the absorption distribution in a section of the examination zone 13, and for example, displays it on a monitor 11. The two motors 2 and 5, the image processing computer 10, the radiation source S and the transfer of the measured values from the detector unit 16 to the image processing computer 10 are controlled by a control unit 7.

Simultaneously, with the acquisition of the measured values a recording of a signal representing the cyclical movement takes place. In the case of a heart examination this can be an ECG signal of an electrocardiograph, which is detected by a sensor 15 applied to the patient. Likewise, this signal is supplied to the image-processing computer 10, in order to select thereby suitable measured values for the reconstruction, which measured values were acquired in such phases of the heart cycle, in which the heart had moved relatively little.

FIG. 2 illustrates the sequence of a measuring and reconstruction method that can be executed with the computer tomograph according to FIG. 1.

After the initialization in block 100 the motors 2 and 5 as well as the radiation source S in the block 101 are switched on. The drive by the two motors 2 and 5 leads to a helical movement of the radiation source relative to the axis of rotation, the conical beam 4 emitted by the radiation source 13 traversing the examination zone 13 and being detected by the detector unit 16. The drive speeds of the two motors 2 and 5 are coordinated with each other so that the distance between two helical windings is smaller by a factor b than the height of the detector arrangement—projected by the radiation source onto the axis of rotation; a suitable value for b lies between 0.15 and 0.3. This provides that so many—redundant—measured values are acquired that a reconstruction of the attenuation of the radiation in the examination zone is possible, although only a fraction of the acquired measured values are taken into account for the reconstruction. Simultaneously, with the acquisition of the measured values the ECG signal is recorded, which is represented in the first row in FIG. 3.

The signals provided by the detector elements are logarithmized, so that they correspond to the line integral of the attenuation of the radiation along the beam path from the radiation source to the respective detector element. The values resulting from the logarithming are designated below as measured values M $(\lambda,\alpha,\gamma)$. $\lambda$ is then the angle position of the radiation source S with respect to the axis of rotation 14 in a plane perpendicular to the axis of rotation and can amount to a multiple of $2\pi$ corresponding to the number of rotations of the radiation source around the axis of rotation. $\alpha$ designates the angle, which the beam path encloses from the radiation source to the detector element, from which the measured value stems, in a plane perpendicular to the axis of rotation 14 with the perpendicular of the radiation source S on the axis of rotation, and $\gamma$ is the angle, which this beam path encloses in a plane comprising the axis of rotation with the perpendicular of the radiation source on the axis of rotation. Thus, measured values are available after the acquisition, which measured values define a cuboid with evenly distributed measuring points in the three-dimensional $\lambda,\alpha,\gamma$ parameter space.

In the next step (block 102) a parallel rebinning takes place, where the measured values M $(\lambda,\alpha,\gamma)$ are transformed into measured values M $(\phi, u, h)$. The parameter $\phi$ then characterizes the orientation of the beam paths projected on a plane perpendicular to the axis of rotation 14, where the relationship holds:

$$\phi=\lambda+\alpha \quad (1)$$

u and h represent the detector co-ordinates of the geometry resulting from the rebinning perpendicular to the axis of rotation, where the relationship holds:

$$u=A\sin(\alpha) \quad (2)$$

$$h=A\tan(\gamma) \quad (3)$$

then A is the distance from the radiation source to the axis of rotation.

If only beam paths running through the axis of rotation are considered first, then the parameter $\phi$ can be allocated to the temporal variation of the ECG signal E, as represented in FIG. 3 in the second row. Thereby, each graduation mark symbolizes a value $\phi$ (or a certain position of the radiation source) to which a multiplicity of measured values with the same parameter $\phi$, but different parameters u and h are allocated. In FIG. 3 only few graduation marks are denoted between two r-peaks. In practice their number, that is the number of the radiation source positions from which measured values have been acquired in this period is, however, greater by decimal powers. The ECG signal, of which only the position of the R-peaks is of interest for the purpose of the invention, can therefore be stored provided that the parameters $\phi_{i1}{}^R, \phi_i{}^R$ and $\phi_{i+1}{}^R$ etcetera belonging to the R-peaks are stored.

In step 103, a rough image CT1 is reconstructed from the measured values that resulted from the parallel rebinning—independent of the fact when the measured values relating to the ECG signal were acquired. The reconstruction can take place based on the filtered back projection. The measured values are pre-weighted with the cosine of the angle $\gamma$ and subjected to a one-dimensional filtering in row direction, while measured values with the same value of $\phi$ and h are each time subjected to a common filtering. The filtered values are then back projected three-dimensionally considering the cone-beam geometry. This back projection or the rough image generated thereby can comprise the entire cross section of the object. However, it can also be limited to a section, which should be selected so large that it certainly comprises the heart of the patient.

In order to accelerate the generation of the rough image, it can be generated with reduced spatial resolution. A possibility therein comprises reconstructing the attenuation on a Cartesian grid, whose grid points have a larger mutual distance, than resulting from the acquisition geometry of the computer tomograph—that is the voxels are increased. However, one can also average the measured values, which are supplied for example by 4×4 detector elements located on a square area of the detector and one can allocate an averaged value to a ray, which connects the center of this area with the radiation source. Then the attenuation is reconstructed with a reduced number of correspondingly larger (and fewer) voxels.

In the following step 104 a region (region of interest—ROI) of interest for the diagnosis is selected from the rough image, which region is the heart of the patient. This selection can take place automatically by means of a suitable image segmenting method or interactively, wherein the user selects characteristic points of the region to be selected.

In step 105 phase points within the heart cycles are predetermined. These phase points define the moments within a heart cycle, in which the heart is almost in a state of rest. The position of a phase point results from the relationship $$\phi_i{}^P=\phi_i{}^R+p(\phi_{i+1}{}^R-\phi_i{}^R) \quad (4)$$

Depending on the heart rate, the parameter p then lies, for example, between 0.35 and 0.45 or between 0.75 and 0.85. The phase points $\phi_{i-1}{}^P, \phi_i{}^P$ and $\phi_{i+1}{}^P$ are entered in the second row of FIG. 3.

In the subsequent step 106 reconstruction windows are optimized, which lie symmetric to the associated phase point, but could have a mutually deviating width. In the second row of FIG. 3 the reconstruction windows $W_{i-1}, W_i$ and $W_{i+1}$ are represented. In principle, the optimization of the window widths takes place as described in the article by Manzke et al, however, limited to the voxels of the selected region ROI.

First all beam paths are then combined that filter a certain voxel at an angle $$\phi=\theta+k\pi \quad (5)$$

Then $\theta$ is an angle between 0 and $\pi$, and k is a non-negative integer (including 0). The highest value of k depends on how often the respective voxel was exposed to radiation at the angle $\phi$. For each value $\phi$ of these beam paths, the temporal distance to the next phase point is determined. The smallest of these distances and the associated phase point are stored. This is repeated for all other angle increments of $\theta$ within an angle area of $\pi$ and subsequently the beam paths on which the other voxels of the selected region ROI were traversed by radiation are handled in a corresponding way.

Then there is a multiplicity of minimum distances of the different voxels for each phase point, from which voxels the largest distance for each phase point is selected. The width of the reconstruction window is double this largest distance. With this optimization it is guaranteed that each reconstruction window is smallest possible, however, on the other hand is large enough, so that there is at least one ray path for each voxel in an angle area of $\pi$, which has traversed this voxel.

However, it is not necessary that the reconstruction windows are symmetrical. From the minimum distances of the voxels of the ROI, one can also select those that have the largest distance from this on both sides of a phase point. These two distances define a window around the phase point that is symmetrical if both distances are the same size and that is otherwise asymmetrical with reference to the phase point.

In step 107 the reconstruction of a CT image of the selected region ROI takes place for which exclusively measured values with a parameter $\phi$ are taken into account, which has been acquired within one of the reconstruction windows. The reconstruction can take place again based on a filtered back projection, while filtered values resulting already in step 102 through filtering of the measured values M $(\phi, u, h)$ can be reverted to—as far as they lie within the reconstruction windows. These values are weighted before the back projection, where, on the one hand, the distance of the associated parameter $\phi$ from the respective phase point $\phi i$ is considered (the larger this distance, so much the smaller the weight of the value) and, on the other hand, there is considered, how many values $\phi$ or $\phi+k\pi$ lie within the various reconstruction windows.

The method is concluded with this reconstruction (block 108).

Still stronger reduced motion artifacts appear or a still further improved temporal resolution result vis-à-vis the method described in the article of Manzke et al. This results from the fact that the reconstruction windows can be smaller, because the optimization is limited to the lowest possible number of voxels through the reconstruction of the rough image in step 103 and by the selection of the region ROI in step 104.

In clinical practice, the representation of a three-dimensional area is not always necessary, but an image slice of the heart is sufficient. In this case, the selected region can be limited to the slice to be represented, which leads to a further reduction of the motion artifacts. However, the steps 104 and 107 must be executed anew if a further image slice is to be generated.

As a rule, the width of the optimized reconstruction windows corresponds to less than 30 percent of a heart cycle. This means that more than 70 percent of the acquired measured values for the CT image generated in step 107 were not needed and that the patient was exposed to a correspondingly high dose of radiation during the acquisition of all measured values. As the position of the phase points or the parameter p (equation 4) can be predetermined already with information of the heart frequency, the dose to which the patient is exposed could be reduced in that, depending on the ECG signal, the radiation source is switched on and off with the acquisition, so that radiation is generated only during a pre-selected, sufficiently large time window which is symmetrical to the phase point.

With the aforesaid optimization of the width of the reconstruction window it remained unconsidered that the measured values with the same parameter $\phi$ were not acquired at exactly the same time, but within a comparatively short time interval. This inaccuracy could be eliminated thereby that the temporal allocation between the ECG signal (or its R-peaks) and the parameter f is not computed or stored, but the time at which the measured values were acquired. The reconstruction window would then correspond to a certain time interval within a heart cycle and it could be optimized in a similar way—with some modifications—as described in connection with step 106:

Then, in step 106, however, the distances between $\phi$ and the phase point $\phi i$ should not be determined, but the temporal distances between the times at which the measured value with the direction $\phi$ was actually measured and the time corresponding with the phase point. The time at which a measured value has been acquired is calculated according to the relationship $$t=T/2\pi(\phi-\arcsin(u/A))\quad(6)$$

where T is the period of rotation, which the radiation source needs for a complete rotation around the axis of rotation. Approximately the following holds:

$$t\approx T/2\pi(\phi-u/A)\quad(7)$$

where the error for a period of rotation of T=0.42 s is below 0.001 s.

The smallest temporal distance to one of the phase times is determined and stored for each voxel for an angle area of the quantity $\pi$. After this has taken place for all voxels of the region ROI, for each phase time the respective largest of the temporal distances determined in such a way is selected and the width of the reconstruction window is fixed at double this distance.

With the subsequent reconstruction in step 107 there must still be checked for each voxel and each angle $\phi$ with the aid of the equation (6) or (7) respectively, which ray traversing the voxel from the direction $\phi+k\pi$ was detected by a detector element in one of the time intervals, which time intervals correspond to the reconstruction windows. Only the measured value that belongs to such a ray is considered with the reconstruction.

It is also possible to use a retrospective gating already with the reconstruction of the rough image. That is, with the reconstruction of the rough image only such measured values are used that were acquired within a window around the various phase points. These windows can have a uniform size, which must be larger than the width of the reconstruction windows, which can be expected. The rough image reconstructed in this way, would represent the heart with better-defined outlines or with fewer motion artifacts respectively, than would be possible without gating.

The invention claimed is:

1. A computer tomography method for the detection of an examination zone, which is exposed at least partly to a cyclical movement of an object, which method comprises the following steps:
    generating a beam traversing the examination zone with a radiation source rotating several times around the examination zone;
    acquiring a set of measured values, which depend on the intensity of the beam beyond the examination zone, with a detector unit during the rotation of the radiation source with simultaneous recording of a signal representing the cyclical movement of the object;
    reconstructing a rough image from the measured values;
    selecting a region within the area represented by the rough image;
    optimizing reconstruction windows in predefinable position within the movement cycles in such a manner that the reconstruction windows are, on the one hand, smallest possible and, on the other hand, so large that each voxel of the region within the reconstruction windows is struck by the beam from an angle range sufficient for the reconstruction; and
    reconstructing an image of the region from the measured values acquired within the reconstruction windows.

2. The method as claimed in claim 1, in which the radiation source emits a conical beam, which is detected by a detector arrangement comprising several detector rows.

3. The method as claimed in claim 2, in which during the acquisition of the set of measured values a helical relative movement detecting a rotation around a rotation axis and a shift parallel to the rotation axis takes place between the radiation source on the one hand and the examination zone on the other hand, the shift being essentially smaller during a 360° rotation around the rotation axis than the height of the detector arrangement projected on the rotation axis.

4. The method as claimed in claim 1, in which the spatial resolution of the rough image is reduced by a low-pass filter or a smoothing method.

5. The method as claimed in claim 1, in which the region is a two-dimensional area.

6. The method as claimed in claim 1, in which depending on the signal representing the cyclical movement, the radiation source is switched on and off with the acquisition of the set of measured values in such a way that radiation is generated only during a pre-selected time window within the movement cycles.

7. The method as claimed in claim 1, in which for the reconstruction of the rough image only measured values are taken into account, which were acquired during a time window with a defined position within the movement cycles.

8. A computer tomography, comprising:
a radiation source, for generating a conical beam traversing an examination zone;
a detector unit coupled with the radiation source;
a driving arrangement to allow an object contained in the examination zone and the radiation source to rotate relative to each other around a rotation axis and/or to be movable parallel to the rotation axis;
a reconstruction unit for the reconstruction of the spatial distribution of the absorption of the measured values acquired by the detector unit within the examination zone, and a control unit for the control of the radiation source, the detector unit, the driving arrangement and the reconstruction unit in accordance with the following steps:
generating a beam traversing the examination zone with a radiation source rotating several times around the examination zone;
acquiring a set of measured values, which depend on the intensity of the beam beyond the examination zone, with a detector unit during the rotation of the radiation source with simultaneous recording of a signal representing the cyclical movement of the object;
reconstructing a rough image from the measured values;
selecting a region within the area represented by the rough image;
optimizing reconstruction windows in predefinable position within the movement cycles in such a manner that the reconstruction windows are, on the one hand, smallest possible and, on the other hand, so large that each voxel of the region within the reconstruction windows is struck by the beam from an angle range sufficient for the reconstruction; and
reconstructing an image of the region from the measured values acquired within the reconstruction windows.

9. A computer-readable medium containing computer executable instruction, which when executed by a computer tomography, instruct a control unit of the computer tomograph for controlling a radiation source, a detector unit of a driving arrangement and a reconstruction unit for detection of an examination zone, which is exposed at least partly to a cyclical movement of an object, in accordance with the following routine:
generating a beam traversing the examination zone with a radiation source rotating several times around the examination zone;
acquiring a set of measured values, which depend on the intensity of the beam beyond the examination zone, with a detector unit during the rotation of the radiation source with simultaneous recording of a signal representing the cyclical movement of the object;
reconstructing a rough image from the measured values;
selecting of a region within the area represented by the rough image;
optimizing reconstruction windows in predefinable position within the movement cycles in such a manner that the reconstruction windows are, on the one hand, smallest possible and, on the other hand, so large that each voxel of the region within the reconstruction windows is struck by the beam from an angle range sufficient for the reconstruction; and
reconstructing an image of the region from the measured values acquired within the reconstruction windows.

10. The method as claimed in claim 1, wherein the selecting of the region is automatically performed by a segmenting method.

11. The method as claimed in claim 1, wherein the selecting of the region is performed interactively, wherein characteristic points of the region are selected.

12. The computer tomograph as claimed in claim 8, wherein the radiation source emits a conical beam, which is detected by a detector arrangement comprising several detector rows.

13. The computer tomograph as claimed in claim 12, wherein during the acquisition of the set of measured values a helical relative movement detecting a rotation around a rotation axis and a shift parallel to the rotation axis takes place between the radiation source on the one hand and the examination zone on the other hand, the shift being essentially smaller during a 360° rotation around the rotation axis than the height of the detector arrangement projected on the rotation axis.

14. The computer tomograph as claimed in claim 8, wherein the spatial resolution of the rough image is reduced by a low-pass filter or a smoothing method.

15. The computer tomograph as claimed in claim 8, wherein the region is a two-dimensional area.

16. The computer tomograph as claimed in claim 8, wherein depending on the signal representing the cyclical movement, the radiation source is switched on and off with the acquisition of the set of measured values in such a way that radiation is generated only during a pre-selected time window within the movement cycles.

17. The computer tomograph as claimed in claim 8, wherein for the reconstruction of the rough image only measured values are taken into account, which were acquired during a time window with a defined position within the movement cycles.

18. The computer tomograph as claimed in claim 8, wherein the selecting of the region is automatically performed by a segmenting method.

19. The computer tomograph as claimed in claim 8, wherein the selecting of the region is performed interactively, wherein characteristic points of the region are selected.

* * * * *